(12) United States Patent
Stevens

(10) Patent No.: US 9,493,255 B2
(45) Date of Patent: Nov. 15, 2016

(54) ERROR REDUCTION IN BLISTER PACKAGING APPARATUS

(75) Inventor: Gerard Stevens, Huntleys Point (AU)

(73) Assignee: Manrex Pty. Ltd., Leichardt (AU)

( * ) Notice: Subject to any disclaimer, the term of this patent is extended or adjusted under 35 U.S.C. 154(b) by 893 days.

(21) Appl. No.: 13/808,230

(22) PCT Filed: Jul. 4, 2011

(86) PCT No.: PCT/AU2011/000831
§ 371 (c)(1),
(2), (4) Date: Jan. 29, 2013

(87) PCT Pub. No.: WO2012/003528
PCT Pub. Date: Jan. 12, 2012

(65) Prior Publication Data
US 2013/0211582 A1   Aug. 15, 2013

(30) Foreign Application Priority Data

Jul. 7, 2010 (AU) .............................. 2010903005

(51) Int. Cl.
| B65B 5/10 | (2006.01) |
| G07F 17/00 | (2006.01) |
| G06F 19/00 | (2011.01) |
| G06Q 10/00 | (2012.01) |
| G06Q 10/08 | (2012.01) |
| G06Q 50/22 | (2012.01) |

(52) U.S. Cl.
CPC ........... B65B 5/103 (2013.01); G06F 19/3456 (2013.01); G06F 19/3462 (2013.01); G06Q 10/00 (2013.01); G06Q 10/087 (2013.01); G06Q 50/22 (2013.01); G07F 17/0092 (2013.01)

(58) Field of Classification Search
CPC ............... B65B 5/103; G06F 19/3456; G06F 19/3462; G07F 17/0092; A61J 2205/10; A61J 2205/30
See application file for complete search history.

(56) References Cited

U.S. PATENT DOCUMENTS

| 4,655,026 | A | * | 4/1987 | Wigoda .............. | G07F 17/0092 53/131.3 |
| 5,713,487 | A | * | 2/1998 | Coughlin ............ | G07F 17/0092 221/2 |
| 5,883,370 | A | * | 3/1999 | Walker et al. ...... | G06F 19/3462 235/375 |
| 5,907,493 | A | * | 5/1999 | Boyer et al. ........ | G06F 19/3462 700/213 |

(Continued)

OTHER PUBLICATIONS

International Search Report PCT/AU2011/00083, completed Sep. 20, 2011, mailed Sep. 26, 2011, 2 pages.

*Primary Examiner* — Stephen F Gerrity
(74) *Attorney, Agent, or Firm* — Chernoff, Vilhauer, McClung & Stenzel LLP

(57) ABSTRACT

An apparatus for reducing human error in loading prescribed medications automatically into blisters (18) of a blister sheet. The operator is provided with a manually-operated controller (15) with which the amount and nature of a particular medication dose can be selected. The operator uses the controller (15) to select the required dosage from a chosen container (13). Each container (13) has a first bar code (14) identifying the nature of the doses it contains. A second bar code is pre-printed on a header sheet (4) which is destined to be attached to the blister sheet after its blisters have been loaded. The second bar code contains information identifying the patient and the contents of the various blisters. A comparator (12) responds to a lack of coincidence between the first and second barcode, by flashing the screen to indicate to the operator that an error has been made.

5 Claims, 1 Drawing Sheet

(56) References Cited

U.S. PATENT DOCUMENTS

| | | | | |
|---|---|---|---|---|
| 5,963,453 | A * | 10/1999 | East | G06F 19/3462 53/493 |
| 6,318,630 | B1 * | 11/2001 | Coughlin et al. | G06F 19/3462 235/375 |
| 7,225,597 | B1 * | 6/2007 | Knoth | B65B 5/103 53/244 |
| 7,454,880 | B1 * | 11/2008 | Austin et al. | G06F 19/3462 53/131.2 |
| 8,295,977 | B2 * | 10/2012 | Yuyama et al. | G07F 17/0092 700/236 |
| 2002/0070226 | A1 * | 6/2002 | Liff et al. | G06F 19/3462 221/9 |
| 2002/0093189 | A1 * | 7/2002 | Krupa | B42D 15/0053 283/81 |
| 2003/0024212 | A1 * | 2/2003 | Schaefer et al. | B65B 57/14 53/410 |
| 2003/0055531 | A1 * | 3/2003 | Liff et al. | G06F 19/3462 700/235 |
| 2003/0125986 | A1 * | 7/2003 | Collosi | G06F 19/3462 705/2 |
| 2004/0046020 | A1 * | 3/2004 | Andreasson et al. | A61J 1/14 235/385 |
| 2004/0064215 | A1 * | 4/2004 | Greeven et al. | G06F 19/3462 700/235 |
| 2005/0131733 | A1 * | 6/2005 | Lubow | G06F 19/3462 705/2 |
| 2006/0122729 | A1 * | 6/2006 | Murphy et al. | A61J 1/035 700/222 |
| 2006/0253346 | A1 * | 11/2006 | Gomez | G06Q 10/087 705/28 |
| 2007/0084150 | A1 * | 4/2007 | Siegel et al. | B65B 5/103 53/475 |
| 2008/0288105 | A1 | 11/2008 | Mauger et al. | |
| 2008/0288287 | A1 * | 11/2008 | Stanners | G06F 19/3462 705/2 |
| 2008/0300718 | A1 * | 12/2008 | Austin et al. | G06F 19/3462 700/235 |
| 2009/0138122 | A1 * | 5/2009 | Wagner | G06F 19/327 700/226 |
| 2009/0152291 | A1 * | 6/2009 | Ohmura et al. | A61J 7/0084 221/197 |
| 2009/0173745 | A1 * | 7/2009 | Parrish | G07F 17/0092 221/2 |
| 2009/0173779 | A1 * | 7/2009 | Szesko et al. | G06F 19/3462 235/375 |
| 2009/0210247 | A1 * | 8/2009 | Chudy et al. | G06F 19/3462 705/2 |
| 2009/0321465 | A1 * | 12/2009 | Knoth et al. | G07F 17/0092 221/1 |
| 2010/0030667 | A1 * | 2/2010 | Chudy et al. | G06F 19/3462 705/28 |

* cited by examiner

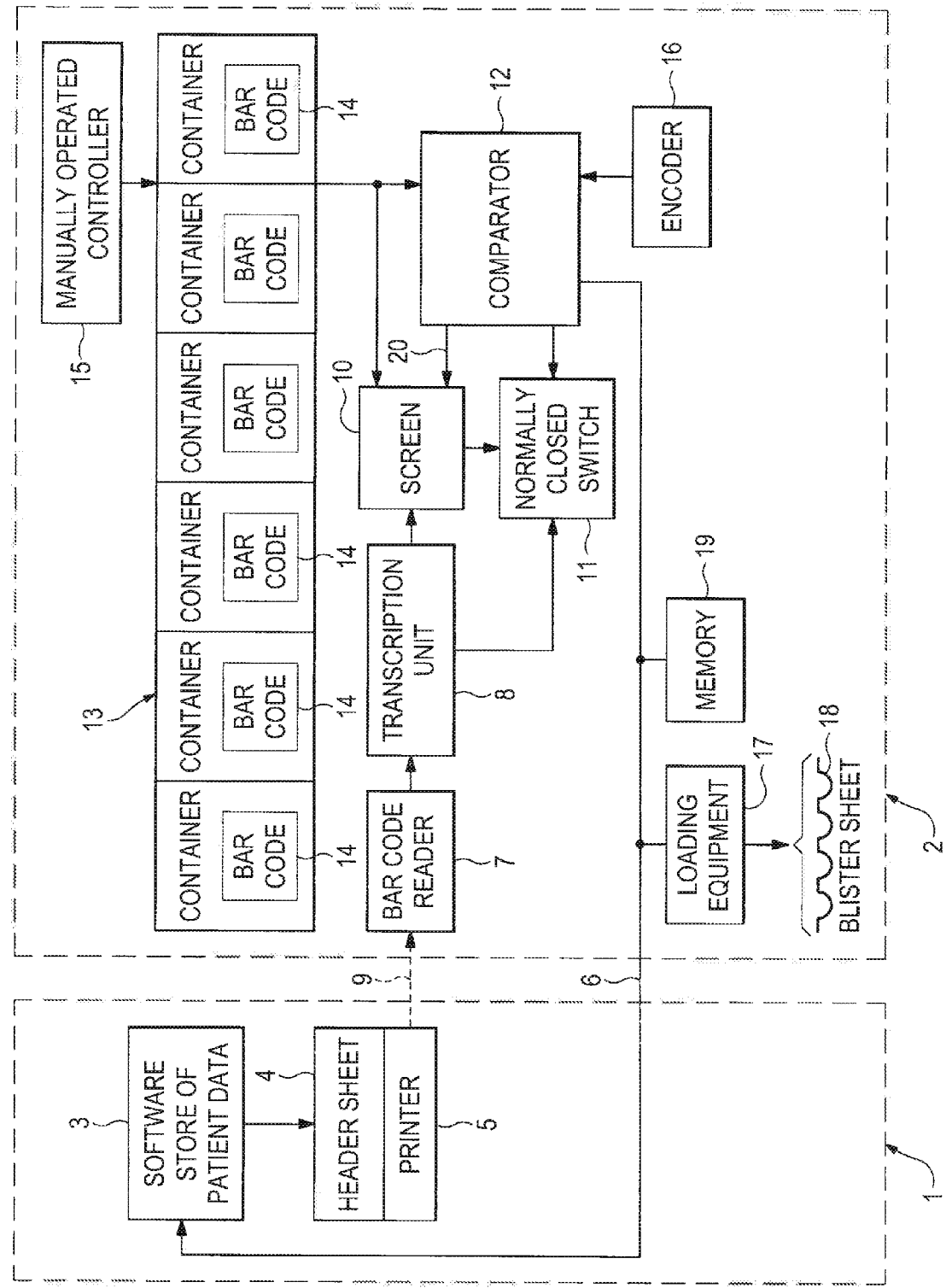

ERROR REDUCTION IN BLISTER PACKAGING APPARATUS

CROSS-REFERENCE TO RELATED APPLICATION

This is a national stage application filed under 35 USC 371 based on International Application No. PCT/AU2011/000831 filed Jul. 4, 2011, and claims priority under 35 USC 119 of Australian Patent Application No. 2010903005 filed Jul. 7, 2010.

FIELD OF THE INVENTION

This invention relates to reducing the incidence of human error in the packaging of prescribed doses of medication in a blister ultimately destined to form part of a blister package.

STATE OF THE ART

Amongst the sources of error in the packaging of a blister by a technician working under the direction of a pharmacist, are the following: the packaging of more medication doses than a doctor has prescribed for a patient; the omission of prescribed doses during packaging; or, an incorrect dose which visually resembles a prescribed dose, being packaged by mistake. Although a pharmacist will normally check the correctness of the prescribed doses in a loaded blister package, studies have shown that the reliance on such checking is not totally successful in removing packaging errors.

OBJECT OF THE INVENTION

An object of this invention is to reduce the risk of such errors occurring.

The Invention

In accordance with the present apparatus for loading blisters of a blister sheet with doses of prescribed medications to be administered to a patient, includes: software for storing a first bar code providing patient-specific data giving the identity of the patient and the nature of and quantity of prescribed medication doses to be administered; equipment for printing a header sheet displaying the first bar code and which is to be applied to the blister sheet after it has been loaded with the prescribed medications; containers respectively for storing medication doses of a particular type required by the patient; a second bar code associated with each container and signifying the medication doses it contains; a bar code reader identifying from the second bar code the selection of the container from which a prescribed medication dose is to be supplied; a comparator which responds to a failure of coincidence between the first bar code and the second bar code; a signal generator providing a fault signal if there is a failure of such coincidence; and, circuitry for preventing the loading of the blister package until a fault indicated by the signal generator has been rectified.

Preferred Feature of the Invention

Preferably the fault signal is a visual one. Conveniently the operator of the apparatus, or an operating means serving the equivalent function, views on a screen the information concerning the nature and quantity of each medication dose which has been read from the bar code on the header sheet. This information is suitably provided as a list on the screen and each prescribed medication appears in one line on the screen, suitably in a single colour. When the correct medication and number of doses from a chosen container have been selected, a change in the colour of the corresponding line on the screen may be arranged to change to a contrasting colour to signify to the operator or the operating means that the prescribed medication has been successfully selected so that the operator or operating means can move to the next line on the screen.

Should the pharmacist become aware of more recent information concerning the medication profile of the patient than is given by the stored bar code, or the use of an acceptable alternative or prescribed medication to the one appearing on the screen, this information can be drawn to the operator's attention and the apparatus can then print a new, updated header sheet. The updated information can also be fed back into the patient profile software so that it will be automatically recorded in the header code.

With the apparatus of the invention a record can be kept of the faults which occur and the competence of the operator or operating means in handling the apparatus. In the case where an operating technician is involved, this will provide the pharmacist with information concerning the reliance that can be placed on the operating technician or whether further training in the use of the apparatus is required.

It will be appreciated that the reading of the bar code from the header sheet provided by the software, can be carried out by a hand-held reader. However the invention is equally applicable to a fully automated apparatus operated by the software so that a technician operating the apparatus, or operating means serving the same function as the technician but automatically, can perform a monitoring function rather than actually initiating extraction of the medication doses from the containers. The selection of the appropriate containers from which the required medication doses are to be supplied is then carried out in the absence of any fault signal being generated by the signal generator.

IN THE DRAWING

The invention will now be described in more detail, by way of a preferred embodiment, illustrated in the accompanying block schematic diagram.

DESCRIPTION OF PREFERRED EMBODIMENT

The apparatus of the drawing is shown in two parts 1 and 2 each of which appears within a rectangular pecked outline. In practice, the two parts 1 and 2 may be combined into a single unit, or they may be separated from one another but nevertheless form parts of a single installation with a visual link 9 extending between them, as illustrated.

Part 1 of the apparatus contains a software store 3 holding patient-specific data relating to the identity of each patient and the nature and quantity of medication which a doctor has prescribed for the particular patient in question. This data is stored in a way enabling it to be printed out as a bar code on a header sheet 4 produced by a printer 5. The header sheet is destined to be applied to a blister sheet after being checked by a pharmacist to ensure it represents the latest information relating to the patient's medication. Where the two parts of the apparatus form a single piece of equipment, the printer 5 and the visual link 9 are omitted and the bar code data read from the header sheet 4 is instead fed directly into part 2 of the apparatus. A feedback loop 6 extending between the parts 1 and 2 enables the bar code data in the software store 3 to be updated by way of manually-operated encoder/6 under the control of a supervising pharmacist if it appears that the data in the store 3 no longer represent the latest prescribed medication profile of the patient.

Reverting to the diagram, part 2 of the apparatus includes a bar code reader 7 for reading the bar code on the header sheet produced by the printer 5. The list of medication doses and their quantities are extracted from the bar code by a transcription unit 8 which presents this medication information and appropriate patient identification information, in one colour on a screen 10. This is located at a position where it can be monitored by the operator of the apparatus. The transcription unit 8 also supplies the information by way of a normally-closed switch 11 to a comparator 12. The switch 11 is controlled by the screen 10 and will open to block the transmission of signals from the transcription unit 8 to the comparator 12 if a fault is suspected or if updating of the information is required.

The operator normally works from a group of containers 13 each of which carries a unique barcode 14 to identify its contents. The operator works from the information displayed on the screen 10 and selects a particular container 13 from which medication doses are to be extracted, by the use of a manually operated controller 15 including a second bar code reader. Signals relating to the identity of the selected container 13 and the quantity of doses extracted from it as selected by the operator, are supplied to the comparator 12 and also to the screen 10.

If there is coincidence between the number and nature of doses selected by the operator to be supplied by the container 14, and the corresponding bar code information held in the transcription unit 8, this will be denoted by a colour change on the screen 10. The switch 11 will remain closed and the comparator 12 will respond to this coincidence by sending a no-fault signal back through the line 20 to the screen 10. Circuitry in the screen then responds to the coincidence by changing the colour of the selected medication displayed on the screen to a contrasting colour. Switching the colour from red to green is the preferred colour change.

The operator responds to a change in colour by moving to the next line in a column of medications lines presented on the screen 10. The above process is then repeated for each line of the column of lines displayed on the screen.

Should the comparator 12 detect a lack of coincidence between a line of medication doses displayed on the screen and originating from information provided by the transcription unit 8, and the medication doses selected by the operator to be supplied from a particular container 13, an error signal is generated. This is fed through the line 20 to the screen. Immediately this occurs, the circuitry in the screen 10 opens the switch 11 and the displayed line on the screen 10 starts to flash to warn the operator that an error has been detected or that there is a need to update the information displayed on the screen. Such updating can be carried out by manually-operated controller 16 under the control of a supervising pharmacist. When the updating is completed, the pharmacist sends a no-fault signal from the controller 16 to the comparator 12 which responds by providing the updating information to the screen 10. This allows the operator of the apparatus, who may be a technician, to move to the next line displayed on the screen 10.

The change in colour of the screen from red to green and there being no flashing of lines occurring, means that the blister cavities can be safely loaded with the correct medication doses. If appropriate, the comparator sends a signal through the feedback line 6 to the software store 3 to update it with the latest information concerning the patient's medication profile. The comparator 12 also initiates operation of equipment 17 which responds by commencing automatic loading of the blister cavities of a blister sheet 18 with the selected and correct medication doses. The comparator 12 also instructs the store 3 to retain the latest bar code representing the updated and new patient's profile. The completion of these various steps undertaken by the comparator is noted for record purposes by a memory 19.

The invention claimed is:

1. Apparatus for loading blister cavities of a blister sheet with doses of prescribed medications to be administered to a patient, comprising:
   software for storing a first bar code providing patient-specific data giving the identity of the patient and the nature of and quantity of prescribed medication doses to be administered;
   equipment for printing a header sheet that displays the first bar code and which is to be applied to the blister sheet after the blister sheet has been loaded with the prescribed medications;
   a first bar code reader arranged to read the bar code from the header sheet;
   a plurality of containers for storing respective medication doses of a particular type required by the patient;
   a respective second bar code associated with each container and signifying the medication doses each container contains;
   a second bar code reader identifying from a respective second bar code a respective one of the containers from which a prescribed medication dose is to be supplied;
   a comparator which responds to a failure of coincidence between the first bar code and the second bar code;
   a signal generator providing a fault signal if there is a failure of such coincidence; and,
   circuitry for preventing the loading of the blister sheet until a fault indicated by the signal generator has been rectified.

2. Apparatus as set forth in claim 1, divided into a first part and a separate second part interconnected by a visual link extending between a position of display of the first bar code on the first part of the apparatus, and the first bar code reader, included in the second part of the apparatus for reading the first bar code.

3. Apparatus as set forth in claim 1 including a screen connected to display to an operator in one colour details of medications prescribed for a particular patient and obtained from the first bar code information, and connections for altering a display of details of a particular medication to a different colour on the screen if coincidence is detected between medication information contained in the first barcode and medication information contained in the second bar code.

4. Apparatus as set forth in claim 3, in which prescribed medication information relating to intended contents of each blister cavity is provided on the screen in the form of a list having each prescribed medication occupying a different line in the list.

5. Apparatus as set forth in claim 1, divided into a first part and a separate second part interconnected by an electrical connection extending between a position of display of the first bar code on the first part of the apparatus, and the first bar code reader, included in the second part of the apparatus for reading the first bar code.

* * * * *

UNITED STATES PATENT AND TRADEMARK OFFICE
CERTIFICATE OF CORRECTION

| | | |
|---|---|---|
| PATENT NO. | : 9,493,255 B2 | Page 1 of 1 |
| APPLICATION NO. | : 13/808230 | |
| DATED | : November 15, 2016 | |
| INVENTOR(S) | : Stevens | |

It is certified that error appears in the above-identified patent and that said Letters Patent is hereby corrected as shown below:

In the Specification

Column 4 Line 54: first bar-code should read -- first bar code --

Signed and Sealed this
Ninth Day of January, 2018

Joseph Matal
*Performing the Functions and Duties of the*
*Under Secretary of Commerce for Intellectual Property and*
*Director of the United States Patent and Trademark Office*